United States Patent [19]

Silver et al.

[11] Patent Number: 4,931,386

[45] Date of Patent: Jun. 5, 1990

[54] METHOD AND COLLAGEN COATED SLIDE FOR ASSAYING COLLAGENASE

[75] Inventors: Frederick H. Silver, R.D. #1, Box 1128, Echo Lake, Bangor, Pa. 18103; Ira B. Lamster, 430 Carlton Rd., Wyckoff, N.J. 07841

[73] Assignees: Frederick H. Silver, Bangor, Pa.; Ira B. Lamster, Wyckoff, N.J.

[21] Appl. No.: 128,099

[22] Filed: Dec. 3, 1987

[51] Int. Cl.$^5$ .................... C12Q 1/38; C12M 1/00
[52] U.S. Cl. ........................ 435/23; 435/287; 435/317.1; 435/805; 435/810; 530/356
[58] Field of Search .............. 435/4, 23, 24, 287, 435/317.1, 805, 810; 530/356

[56] References Cited

U.S. PATENT DOCUMENTS

| | | | |
|---|---|---|---|
| 3,649,347 | 3/1972 | Battista | 117/144 |
| 3,730,843 | 5/1973 | McKie, Jr. | 195/103 |
| 3,753,099 | 8/1973 | Kleinberg et al. | 324/61 |
| 3,985,620 | 10/1976 | Karges | 195/103 |
| 4,066,509 | 1/1978 | Ceska | 195/103.5 |
| 4,138,394 | 2/1979 | Sakakibara et al. | 260/112.5 |
| 4,176,009 | 11/1979 | Sakakibara | 435/24 |
| 4,357,142 | 11/1982 | Schall, Jr. et al. | 23/230 |
| 4,425,428 | 1/1984 | Weingarten | 435/23 |
| 4,443,367 | 4/1984 | Weingarten | 260/112.5 |
| 4,466,919 | 8/1984 | Weingarten | 260/112.5 |
| 4,507,389 | 3/1985 | Weingarten | 435/23 |
| 4,569,907 | 2/1986 | Weingarten et al. | 435/23 |
| 4,572,901 | 2/1986 | Ceriani et al. | 436/528 |

FOREIGN PATENT DOCUMENTS

| | | |
|---|---|---|
| 176246 | 4/1986 | European Pat. Off. . |
| 2204159 | 9/1987 | Japan .................... 435/23 |

OTHER PUBLICATIONS

Farber et al., "Int. J. Macromol", vol. 8, pp. 37-42, (Feb. 1986).
Weadock et al., "Biomat. Med. Dev., Art. Org.", vol. 11, pp. 293-318 (1983-1984).
Advanced Clinical Technologies, Periocheck Instruction Manual (1986).
Silver et al., "Jour. Biomed. Materials Research", vol. 13, pp. 701-716 (1979).
Silver et al., "Int. J. Biol. Macromol", vol. 6, pp. 125-132 (Jun. 1986).

*Primary Examiner*—David M. Naff
*Attorney, Agent, or Firm*—Ostrolenk, Faber, Gerb & Soffen

[57] ABSTRACT

The collagenolytic activity of mammalian biologic fluids is assayed by obtaining a specimen of such fluid; applying the fluid to a collagen film bonded to a surface such as that of a glass slide; incubating the slide; washing the slide; staining the slide with a dye, and determining the extent of dissolution of the collagen film from the unstained areas of the slide. The slide is preferably prepared by blending insoluble collagen with a solution of HCl to form a dispersion; applying the dispersion to the slide surface; drying the slide; and baking the slide to cross-link the collagen and bond it to the slide surface. The dispersion applied to the slide contains collagen particles having sizes of at least 1 micron and preferably at least 20 microns. The assay procedure is particularly useful for the determination of the collagenase activity of gingival crevicular fluid (GCF), in which case the fluid specimen is obtained on an absorbent medium such as a filter paper strip. An aspect of the invention is the provision of a kit suitable for use in dental offices which includes absorbent strips; one or more slides having collagen bonded to the surface thereof; and a container of a dye solution capable of staining collagen. The kit may also include one or more collagenase standards.

11 Claims, 1 Drawing Sheet

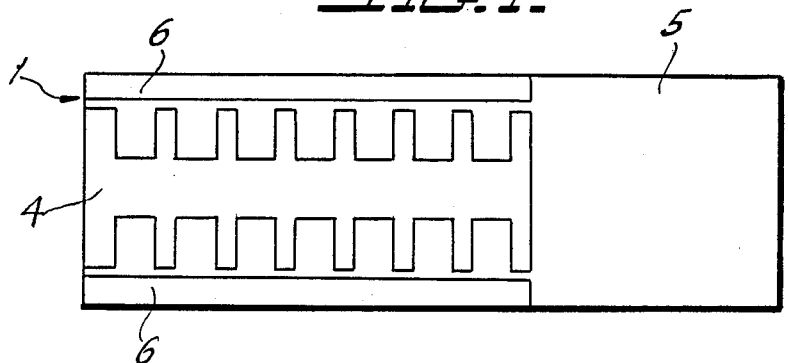
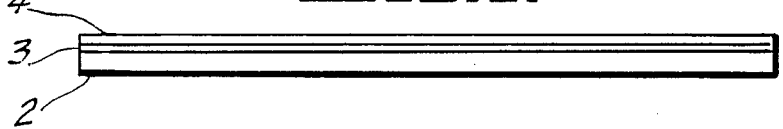
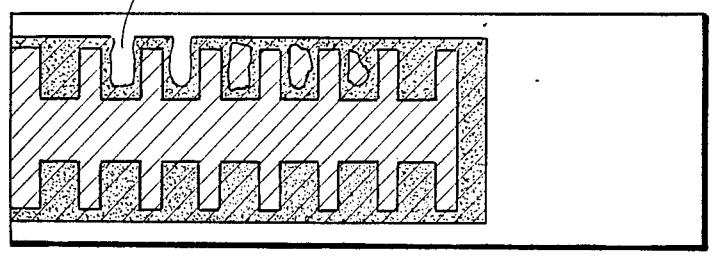
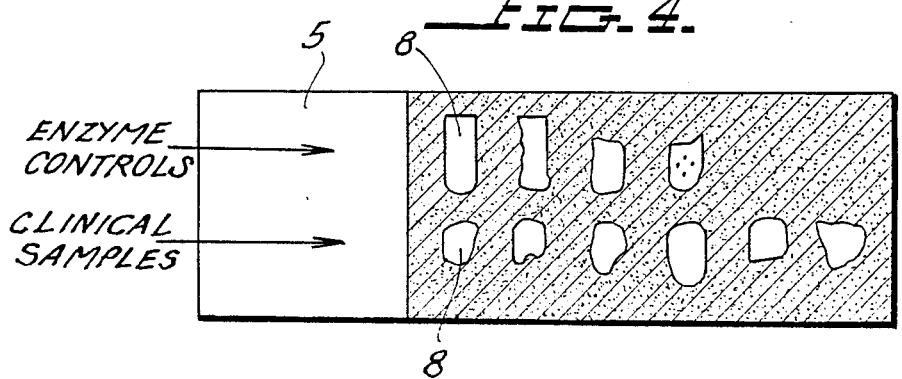
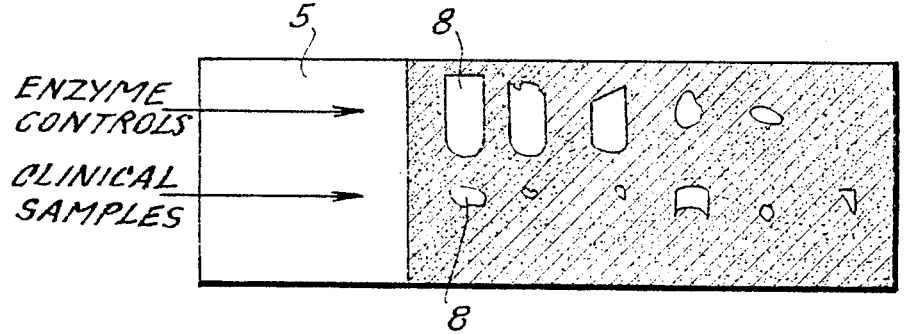

METHOD AND COLLAGEN COATED SLIDE FOR ASSAYING COLLAGENASE

BACKGROUND OF THE INVENTION

This invention relates to method and means for assaying collagenase in mammalian biologic fluids. More particularly, it relates to such method and means involving the use of collagen to quantitate the collagenase activity of gingival crevicular fluid, hereinafter referred to as GCF.

With the realization that standard clinical measurements of human periodontal disease are not indicative of current loss of clinical periodontal attachment or predictive of future loss of attachment (Haffajee, A. D., Socransky, S. S. and Goodson, J. M.: Clinical parameters or predictors of destructive periodontal disease activity, *J. Clin. Periodontol.* 10:257, 1983), attention has focused on the need for sensitive measures of active periodontal disease (Polson, A. M. and Goodson, J. M.: Periodontal diagnosis: current status and future needs, *J. Periodontol.* 56:25, 1985). Among the possible approaches for such a diagnostic test, biochemical analysis of GCF has received considerable attention (Fine, D. H. and Mandel, I. D.: Indicators of periodontal disease activity: an evaluation, *J. Clin. Periodontol.* 13:533, 1986). Study of the volume and constituents of the fluid that characterize periodontal health and disease has been conducted for almost 30 years.

Proteolytic enzymes are among the constituents of GCF that have been examined for their diagnostic potential. Among these, collagenase is of particular interest since collagen is the major structural protein of the periodontium, and loss of collagen is characteristic of both gingivitis and periodontitis (Narayanan, A. S. and Page, R. C.: Connective tissue of the periodontium: a summary of current work, *Col. Rel. Res.* 3:33, 1983.) Previous studies have correlated increased collagenase activity in GCF with increased gingival inflammation (Ohlsson, K., Olsson, I. and Tynelius-Bratthal, G.: Neutrophil leukocyte collagenase, elastase and serum protease inhibitors in human gingival crevices, *Acta Odont. Scand.* 31:51, 1973; Golub, L. M., Siegel, N., Ramamurthy, C. and Mandel, I.: Some characteristics of collagenase activity in gingival crevicular fluid and its relationship to gingival disease in humans, *J. Dent. Res* 55:1049, 1976). Furthermore, a study of beagle dogs with ligature-induced periodontitis indicated that collagenolytic activity in GCF was correlated with loss of attachment (Kryshtalskyj, E., Sodek, J. and Ferrier, J. M.: Correlation of collagenolytic enzymes and inhibitors in gingival crevicular fluid with clinical and microscopic changes in experimental periodontitis in the dog. *Archs. Oral Biol.* 31:21, 1986). Nevertheless, quantitation of collagenase activity in biologic fluids frequently involves the use of radio labelled collagen substrates ($^3$H-collagen, $^{14}$C-collagen) or gel electrophoresis to identify collagen breakdown fragments (Ohlsson et al., Ibid.; Golub et al., Ibid.; Kryshtalskyj et al., *Ibid*. These approaches cannot be conveniently incorporated into an in-office test kit to be used by the dentist or dental hygienist.

We have developed an approach to measuring collagenolytic activity in small volumes of mammalian biologic fluid. This test is based on degradation of Type I collagen that is bound to an inert surface, and is semi-quantitative by evaluating the zone of collagen clearance. The specificity of this reaction has been studied by examining the effect of different enzymes on the substrate. It has been determined that collagenase will rapidly degrade the film, trypsin will degrade the film only at very high enzyme concentrations and pepsin and various ground-substance degrading enzymes have essentially no effect on the film.

SUMMARY OF THE INVENTION

The invention involves a method for assaying the collagenolytic activity of mammalian biologic fluids comprising (a) obtaining a specimen of such fluid; (b) applying that fluid to a collagen film bonded to a surface such as that of a glass slide or a slide of a plastic of high surface energy so that collagen will bond to it; incubating the slide; washing it; staining it with a dye, such as Coomasie Brilliant Blue, capable of staining collagen; and determining the extent of dissolution of the collagen film from the unstained areas of the slide, e.g. from the degree of light transmission through the film. This can be done either visually or with a spectrophotometer employing light of a non-absorbing wavelength. The collagen film is preferably cross-linked and is bonded to the surface of the slide preferably by baking. The degree of cross-linking and the subsequent incubation time may be controlled by varying the baking time and/or the thickness of the film.

The slide is preferably prepared by (a) blending insoluble collagen with a solution of HCl to form a dispersion; applying the dispersion to the slide surface; drying the slide, as by air drying at room temperature; and baking the slide to cross-link the collagen and bond it to the slide surface. The dispersion applied to the slide preferably contains collagen particles having sizes of at least 1 micron and preferably at least 20 microns. The slide may be divided by a mask into compartments.

The assay procedure is particularly useful for the determination of the collagenase activity of gingival crevicular fluid (GCF), in which case the fluid specimen is obtained on an absorbent medium such as a filter paper strip. However, it may also be applied to the collagenase assay of other tissue fluids, including sinovial fluid, lung lavage fluid, serous exudates, etc. In these cases, the fluid specimen may be applied directly to the slide without first being absorbed on an absorbent medium.

An aspect of the invention is the provision of a kit suitable for use in dental offices which includes (a) absorbent strips, e.g., filter paper; one or more slides having collagen bonded to the surface thereof; and a container of a dye solution capable of staining collagen. The kit may also include one or more standardized collagenase impregnated filter paper strips, containers of standard collagenase solutions, or other collagenase standards.

BRIEF DESCRIPTION OF THE DRAWING

In the appended drawings:

FIG. 1 is an upper surface view of a glass slide employed in this invention;

FIG. 2 is a vertical view of such slide;

FIG. 3 is an upper surface view of such slide as it appears following an assay with test specimens.

FIG. 4 is an upper surface view of another slide embodiment as it appears following an assay of a patient with high GCF collagenolytic activity.

FIG. 5 is an upper surface view of such embodiment as it appears following an assay of a patient with low GCF collagenolytic activity.

DETAILED DESCRIPTION OF THE INVENTION

This invention involves a collagenolytic assay based on the dissolution of a cross linked collagen substrate that is bound to an inert surface, more specifically, that of a glass slide. More particularly, the invention involves:

(1) Bonding of soluble or insoluble collagen to the surface of a glass slide using a heat baking step; the collagen film cannot be removed with a neutral pH aqueous solvent after baking. During the baking step the collagen is cross-linked by dehydration, forming synthetic peptide bonds.

(2) The degree of cross-linking of the collagen film and the subsequent time for dissolution after contact with a collagenolytic enzyme is controlled by varying the baking time as well as the film thickness.

(3) The collagenolytic assay can be quantitatively interpreted by measuring the dissolution of an unknown specimen of GCF, e.g. by comparing it with a collagenase standard. The incubation time can be varied by controlling the incubation temperature.

(4) The extent of dissolution of the collagen film is related to the collagenolytic activity of GCF.

GCF is collected from the mesiobuccal crevice of preferably at least the four most distal teeth in each quadrant. Precut methyl-cellulose filter paper strips having end portions encased in plastic holders (Harco Electronics, Tustin, California) are inserted into the crevice at a 45-degree angle until mild resistance is felt and held in place for 30 seconds. The strips are then placed on the prepared collagenolytic test slides and assayed as described below.

The invention is illustrated by the following Examples:

EXAMPLE 1

Collagen Dispersion Preparation

Ground bovine corium containing particles of 20 microns or larger, obtained from Devro, Inc., Somerville, N.J., is washed with distilled water and isopropanol and then lyophilized. The resulting washed lyophilized collagen is ground into a powder using a Wiley mill. The ground powder is screened through a series of sieves with openings that are in excess of 1 micron in diameter, e.g., a 40 mesh screen. The material used in preparing the dispersion is the fraction that does not pass through the sieve openings.

The collagen dispersion is prepared for coating the glass slides in the following manner:

(1) A 1N solution of HCl is slowly added to 120 ml of distilled water until the pH is 2.0 at room temperature. The contents of the beaker are then emptied into a 200 ml graduated cylinder.

(2) 1.2 grams of powdered insoluble collagen as obtained above is added to a Waring blender along with the 120 ml of HCl pH 2.0. The 1% w/v dispersion is blended at high speed (5000 r.p.m.) for 3 minutes, the blending being carried out gently enough to maintain particle size. Particle sizes of one micron or greater are needed in order to produce films that have substantial mechanical stability.

(3) The dispersion is emptied into a sidearm flask (600 ml). A vacuum of 100 microns is applied to the dispersion at room temperature until the air bubbles are removed. This procedure may require up to 15 minutes. The vacuum is then removed and the dispersion is ready for slide coating.

EXAMPLE 2

Slide Coating Procedure (1) RITE-ON MICROSLIDES (Clay Adams CAT. NO. 3050) are dipped by hand into the collagen dispersion. To prevent coating both sides of the slide, tape is applied to one side of the slide. The film thickness deposited on the slide depends on the collagen concentration. Thin films are prepared using a collagen dispersion concentration of 0.25% w/v. Therefore the dispersion prepared above would be diluted 1 to 4 with HCl pH 2.0.

(2) The slides are allowed to air dry under a hood or in a dust-free environment.

(3) The slides are washed in distilled water by dipping into a beaker several times.

(4) The slides are again dried in a dust free environment.

(5) The slides are baked for 30 minutes at 110° C. in a circulating air oven.

(6) The tape is peeled off the uncoated side of each slide and the coated side of the slide is marked.

(7) The slides are stored at room temperature until they are required for testing.

The slides are preferably prepared with a mask or divider to allow compartmentalization of each sample. Such a slide is illustrated in FIGS. 1 and 2 of the appended drawing. As shown in these figures, the prepared slide 1 consists of a standard glass slide of rectangular shape 2 having a thin film of collagen 3 bonded to the upper surface thereof. The slide is divided into compartments by a mask 4, a space 5 being provided at one end, here shown on the right side, for labeling. Seven compartments are shown in each row. This allows for one sample to be analyzed from each tooth in a quarter of the mouth.

The mask, suitably of a plastic film such as polyethylene, polypropylene, polyurethane, etc., is suitably applied to the upper surface of the collagen coated slide using a water and alcohol insoluble adhesive such as an epoxy. Strips of double-sided tape 6 (e.g., tape having adhesive on both sides) may be attached along the top and bottom margins of the slide to serve as means for anchoring the filter paper strips by the plastic encased end portions thereof.

EXAMPLE 3

Assay Procedure

Assessment of collagenolytic activity in GCF is made by placing the test strips, as obtained above, on the assay slide, and comparing the zone of clearance to the zones of clearance obtained with standard amounts of commercially available collagenase (5.0, 2.5, 1.25, 0.63, 0.32 units of type I collagenase derived from *Clostridium histolyticum* #C-0130; Sigma Chemical Corporation, St. Louis, Missouri). All filter paper strips are placed on the slide using double-sided tape, and 5-7 ul of buffer (saline with 10 mM Tris and 25 mM $CaCl_2$, pH=7.4) are added directly to the strips to assure wetting the surface. The slide is incubated for 2 hours at room temperature (25° C.) under 100% relative humidity. The humidifier consists of a closed petrie dish containing a sponge wetted by distilled water to provide the humidity. After 2 hours, the filter paper strips are removed and the slides are thoroughly washed with distilled water and stained with a Coomasie Brilliant Blue solution (125 ml 2-propanol, 50 ml acetic acid, 250 mg Coomasie Brilliant Blue [type "R", #B-0630; Sigma Chemical Corporation, St. Louis, Missouri] and 500 ml of distilled water) for 1 minute. The slides are rinsed again in distilled water and allowed to dry. Evaluation of the clearance of the collagen gel is then made. Areas of the slide that were not covered with filter paper contain the unaltered gel which retains an intermediate blue color (negative control). The 5.0 units of collagenase standard demonstrates complete clearance of the gel. Grading of GCF collagenolytic activity is on a +5 to 0 scale, corresponding to the 5 collagenase standards and the negative control. All individual GCF samples are scored. For ease of application, the scale may be reduced to 5 (+4 to 0) or 4(+3 to 0) grades.

FIG. 3 shows the results obtained when standardized filter strips were placed in all compartments in the top row except the far left and the slide processed as described above. The strips contained, moving from left to right, 5.0, 2.5, 1.25, 0.63 and 0.32 of bacterial collagenase in 1.0 ul of buffer. The strip applied to the far right compartment of the top row contained only buffer. That time of incubation of the slide in this case was 3 hours at 25° C. The cleared areas 7 are those areas where the collagen on the slide has been degraded by the collagenolytic activity on the strips and hence do not retain the stain. No strips were placed in the bottom row.

FIGS. 4 and 5 illustrate slides which have been used clinically. These slides did not include masks and were used to assay six GCF specimens from each patient following the assay procedure of Example 3. The label area 5 is here shown on the left hand side. The slides were otherwise identical to that shown in FIGS. 1 and 2. FIG. 4 shows a slide used in the test of a patient with high collagenolytic activity and FIG. 5 that of a patient with low collagenolytic activity. Six standardized control filter strips were placed in the top row and six test filter strips (clinical samples) were placed in the bottom row. The control strips contained, reading from left to right, 5.0, 2.5, 1.25, 0.63, 0.32 and zero units of bacterial collagenase in 1.0 ul of buffer. The cleared areas are here labeled 8.

Dyes other than Coomasie Brilliant Blue can, of course, be substituted in the staining step, for example, eosin and hematoxylin.

Although the present invention has been described herein by means of certain specific embodiments, and illustrative examples, it is not intended that the scope thereof be limited in any way thereby, and the invention is capable of various modifications and adaptations, as those skilled in the art will readily appreciate.

We claim:

1. A method for assaying collagenolytic activity of a mammalian biologic fluid comprising:
   (a) obtaining a specimen of said mammalian biologic fluid;
   (b) applying said specimen to a slide having a collagen substrate film bonded to the surface thereof;
   (c) incubating said slide;
   (d) washing said slide
   (e) staining said slide with a solution of a dye capable of staining collagen; and
   (f) determining the extent of dissolution of said collagen substrate from the extent of the unstained areas of the slide; said slide being prepared by a method consisting essentially of:
   (1) blending insoluble collagen with a solution of HCl to form a dispersion, said insoluble collagen consisting of collagen powder which does not pass through sieve openings in excess of 1 micron in diameter; and said blending being carried out gently enough to maintain particle size;
   (2) applying said dispersion without an added chemical cross-linking agent to the surface of a slide; and
   (3) baking said slide, whereby said collagen is cross-linked and bonded to the surface of said slide, in the absence of an added chemical cross-linking agent.

2. The method of claim 1 wherein the degree of cross-linking of said collage and incubating time are controlled by varying the baking time and/or thickness of the collagen substrate film.

3. The method of claim 1 wherein said dye is Coomasie Brilliant Blue.

4. The method of claim 1 wherein said mammalian biologic fluid is gingival crevicular fluid and said specimen is obtained on an absorbent medium.

5. The method of claim 4 wherein said slide is transparent and the determination of the extent of dissolution of said collagen substrate is based on the transmission of light.

6. A slide for assay of collagenolytic activity of multiple samples of gingival crevicular fluid, said slide being prepared by a method consisting essentially of:
   (1) blending insoluble collagen with a solution of HCl to form a dispersion, said insoluble collagen consisting of collagen powder which does not pass through sieve openings in excess of 1 micron in diameter; and said blending being carried out gently enough to maintain particle size;
   (2) applying said dispersion without an added chemical cross-linking agent to the surface of a slide; and
   (3) baking said slide, whereby said collagen is cross-linked and bonded to the surface of said slide, in the absence of an added chemical cross-linking agent; said slide being divided into compartments.

7. An assay kit for collagenolytic activity of gingival crevicular fluid comprising:
   (a) absorbent strips;
   (b) one or more slides having collagen bonded to the surface thereof; and
   (c) a container of a dye capable of staining collagen; said slides being prepared by a method consisting essentially of:
   (1) blending insoluble collagen with a solution of HCl to form a dispersion, said insoluble collagen consisting of collagen powder which does not pass through sieve openings in excess of 1 micron in diameter; and said blending being carried out gently enough to maintain particle size;
   (2) applying said dispersion without an added chemical cross-linking agent to the surface of a slide; and
   (3) baking said slide, whereby said collagen is cross-linked and bonded to the surface of said slide, in the absence of an added chemical cross-linking agent.

8. An assay kit as defined in claim 7 comprising also one or more collagenase standards containing known amounts of collagenase.

9. An assay kit as defined in claim 8 wherein said collagenase standards are collagenase impregnated filter paper strips containing known amounts of collagenase.

10. An assay kit as defined in claim 8 wherein said collagenase standards are standardized collagenase solutions containing known amounts of collagenase.

11. A method of preparing a slide for use in an assay of collagenolytic activity consisting essentially of:

(a) blending insoluble collagen with a solution of HCl to form a dispersion, said insoluble collagen consisting of collagen powder which does not pass through sieve openings in excess of 1 micron in diameter, and said blending being carried out gently enough to maintain particle size;

(b) applying said dispersion without an added chemical cross-linking agent to the surface of a slide; and (c) baking said slide, whereby said collagen is cross-linked and bonded to the surface of said slide, in the absence of an added chemical cross-linking agent.

* * * * *